United States Patent [19]

Sangha

[11] Patent Number: 5,506,114
[45] Date of Patent: Apr. 9, 1996

[54] METHODS AND KITS FOR DETECTING THE PRESENCE OR CONCENTRATION OF BIOLOGICAL ANALYTES

[75] Inventor: Jangbir S. Sangha, Overland Park, Kans.

[73] Assignee: Osborn Laboratories, Olathe, Kans.

[21] Appl. No.: 312,504

[22] Filed: Sep. 26, 1994

Related U.S. Application Data

[63] Continuation of Ser. No. 27,549, Mar. 8, 1993, abandoned, which is a continuation of Ser. No. 832,429, Feb. 7, 1992, abandoned.

[51] Int. Cl.$^6$ .............................. C12Q 1/48; C12Q 1/26; G01N 33/53
[52] U.S. Cl. ............................. 435/15; 435/28; 435/25; 435/810; 435/4; 435/7.92; 435/7.9; 435/7.8
[58] Field of Search .................... 435/15, 4, 16, 435/23, 7.1, 7.9, 7.72, 7.95, 28, 25, 810, 7.92, 7.8

[56] References Cited

U.S. PATENT DOCUMENTS

| | | | |
|---|---|---|---|
| 3,769,173 | 10/1973 | Carroll | 435/24 |
| 3,773,626 | 11/1973 | Bernt et al. | 435/24 |
| 4,208,479 | 6/1980 | Zuk et al. | 435/7.9 |
| 4,258,001 | 3/1981 | Pierce et al. | 435/7.1 |
| 4,472,498 | 9/1984 | Masuda et al. | 436/500 |
| 4,843,013 | 6/1989 | Chiang | 436/8 |
| 4,868,130 | 9/1989 | Hargreaves | 435/7.92 |
| 4,943,526 | 7/1990 | Rauscher et al. | 435/15 |
| 4,975,366 | 12/1990 | Sudo et al. | 435/7.93 |
| 5,037,764 | 8/1991 | Wilk et al. | 435/7.92 |

OTHER PUBLICATIONS

Stedman's Medical Dictionary; 24th Edition, pp. 471, 1153 & 1494, 1990.

Article *Textbook of Clinical Chemistry* by Norbert W. Teitz, W. B. Sanders Philadelphia, PA 1986, pp. 669–678, 721–727, 741–746.

Article *Concise Encyclopedia of Biochemistry*, 2d Ed. Walter De Gruyter, New York 1988, pp. 610–611.

Sigma Chemical Co. Product Literature—*Gammaglutamyltransferase Immunoassay*, pp. 3–10.

Article *Peroxidase* from The Worthington Manual, Worthington Biochemical Corp., Freehold, NJ pp. 254–260 (1988).

Article *Comparison of Chromogens for the Determination of Horseradish Peroxidase as a marker in Enzyme Immunoassay*, from J. Clin Chem Clin Biochem, vol. 19, 1981 pp. 435–439.

Abstract—Brodeur, B R, et al. Protection against infection with Neisseria meningitidis group B serotype 2b by passive immunization with serotype-specific monoclonal antibody. Infect Imm. 1985 Nov;50(2): 510–6. ¶ 1, p. 1.

(List continued on next page.)

Primary Examiner—Michael G. Wityshyn
Assistant Examiner—Louise N. Leary
Attorney, Agent, or Firm—Pretty, Schroeder, Brueggemann & Clark; Stephen E. Reiter

[57] ABSTRACT

Methods for detecting the presence or concentration of an analyte in a matrix by exploiting the specificities of the analyte's antibody and enzyme-substrate are disclosed. The analyte is first extracted from the matrix by binding it to its specific antibody which has been attached to a solid surface. The antibody-bound analyte is then separated from the matrix to remove it from any interfering substances. Next, the antibody-bound analyte is reacted with its specific enzyme-substrate to generate a signal proportionate to the amount of analyte bound to the antibody, which in turn is dependent on the quantity of analyte present in the matrix. Applications of the methods of the present invention to detect the presence and concentration of hemoglobin, a transferase, and a serine protease, are specifically disclosed. Further, kits useful for utilizing the methods of the present invention are also disclosed.

23 Claims, 2 Drawing Sheets

OTHER PUBLICATIONS

Abstract—Chappell, C L, et al. Antibody response to a purified parasite proteinase (SMw32) in Schistosoma mansoni infected mice. Am J. Trop Med Hyg 1988 Jul.;39(1): 66–73. ¶ 2, pp. 1–2.

Abstract—Croci, D, et al. Quantitative determination of phenobarbital and phenytoin by dry–phase apoenzyme reactivation immunoassay system (ARIS). Ther Drug Monit 1987 Jun.; 9(2): 197–202. ¶ 3, p. 2.

Abstract—Davis, S J, et al. A critical evaluation of a new fluroescence immunoassay system for the measurement of serum phenytoin concentrations. Ann Clin Biochem 1983 Sep.; 20(Pt 5): 274–9. ¶ 4, p. 3.

Abstract—Davis, S J, et al. Measurement of serum theophylline concentrations using a modified Ames TDA system. Ther Drug Monit 1983; 5(4): 479–84. ¶ 5, p. 3.

Abstract—Graver, F A, et al. Generation of a monoclonal antibody specific for Hb G–Philadelphia [alpha 2(68) (E17)Asn——Lys beta 2] and development of an immunoassay. Hemoglobin 1988; 12(2): 125–36. ¶ 7, p. 4.

Abstract—Garver, F A, et al. Screening for hemoglobins S and C in newborn and adult blood with a monoclonal antibody in an ELISA procedure. Blut 1990 Jun.; 60(6): 334–8. ¶ 8, p. 5.

Abstract—Katnik, I, et al. Enzyme immunoassay to measure low levels of haptoglobin in biological fluids. J. Immunoassay 1990; 11(4): 503–17. ¶ 9, p. 5.

Abstract—Kiefer, C R, et al. Characterization and application of a monoclonal antibody with dual specificity for hemoglobins S and C. J Lab Clin Med 1988 Dec.; 112(6): 760–4. ¶ 10, p. 6.

Abstract—Kiefer, C R, et al. Negative screening for sickle cell diseases with a monoclonal immunoassay on newborn blood eluted from filter paper. J Lab Clin Med 1990 Dec.; 116(6): 826–30. ¶ 11, p. 6.

Abstract—Klasen, E A, et al. Development of a screening system for detection of somatic mutations. II. The use of peptides and insoluble protein fragments in a non–competitive solid–phase enzyme immunoassay. J. Immunol Methods 1983 May 13; 59(3): 281–7. ¶ 12, p. 7.

Abstract—Lee, B M, et al. Quantitation of protein adducts as a marker of genotoxic exposure: immunologic detection of benzo[a]pyrene—globin adducts in mice. Carcinogenesis 1988 Oct.; 9(10): 1772–7. ¶ 13, pp. 7–8.

Abstract—Lehmann, DR. Improvements to the SYVA fluoroescence energy transfer immunoassay for digoxin. Clin Biochem 1985 Oct.; 18(5): 300–3. ¶ 14, p. 8.

Abstract—McBride, J H, et al. Creatine kinase MB measured by fluorometric enzyme immunoassay and immunochemiluminescence. Ann Clin Lab Sci 1991 Jul.–Aug.; 21(4): 284–90. ¶ 15, pp. 8–9.

Abstract—Moscoso, H, et al. Enzyme immunoassay for the identification of hemoglobin variants. Hemoglobin 1990; 14(4): 389–98. ¶16, p. 9.

Abstract—Moscoso, H, et al. Monoclonal antibody–based immunoassays for serum myoglobin quantification in acute myocardial infarction. J Clin Lab Anal 1990; 4(6): 437–42. ¶ 17, pp. 9–10.

Abstract—Moscos, H, et al. Quantification of hemoglobins S, C, and F by a magnetic affinity immunoassay. Clin Chem 1988 Ma; 34(5): 902–5. ¶ 18, p. 10.

Abstract—Notomi, T, et al. Radioimmunoassay development for human neuron–specific enolase: with some clinical results in lung cancers and neuroblastoma. Tumour Biol 1985; 6(1): 57–66. ¶ 19, pp. 10–11.

Abstract—O'Rahily, S, et al. Haemolysis affects insulin but not C–peptide immunoassay. Diabetologia 1987 Jun.; 30(6). ¶ 20, p. 11.

Abstract—Ohe, Y, et al. Radioimmunoassay of glycosylated albumin with monoclonal antibody to glucitol–lysine. Clin Chim Acta 1987 Nov. 16; 169(2–3): 229–38. ¶ 21, p. 11.

Abstract—Opheim, K E, et al. Particle–enhanced turbidimetric inhibition immunoassay for #! eophylline evaluated with the Du Pont aca. Clin Chem 1984 Nov.; 30(11): 1870–4. ¶ 22, p. 12.

Abstract—Ruchel, R, et al. Detection of Candida proteinase by enzyme immunoassay and interaction of the enzyme with alpha–2–macroglobulin. J. Immunol Methods 1983 Jun. 24; 61(1): 107–16. ¶23, p. 12.

Abstract—Senju, O, et al. A new immuno quantitative method by latex agglutination—application for the determination of serum C–reactive protein (CRP) and its clinical significance. J Clin Lab Immunol 1986 Feb.; 19(2): 99–103. ¶ 24, p. 13.

Abstract—Stelling, H P, et al. A comparative study of fecal occult blood tests for early detection of gastrointestinal pathology [see comments]. Comment in: Arch Intern Med 1990 May; 150(5): 945–6. Arch Intern Med 1990 May; 150(5): 1001–5. ¶ 25, pp. 13–14.

Abstract—Takano, E, et al. Enzyme immunoassay of calpain I and calpastatin and its application to the analysis of human erythrocyte hemolysate. J Appl Biochem 1984 Jun.; 6(3): 117–24. ¶ 26, p. 14.

Abstract—Tatsu, Y, et al. Homogeneous chemiluminescent immunoassay based on complement–mediated hemolysis of red blood cells. Anal Chem 1990 Oct. 1; 62(19): 2103–6. ¶ 27, pp. 14–15.

Abstract—Yamamoto, R, et al. Enzyme Immunoassay for antibodies to thyroxine in human serum using synthesized antibody as a calibrator. J Immunol Methods 1988 Dec. 9; 115(2): 263–8. ¶ 28, p. 15.

Abstract—Zenke, M, et al. v–erbA specifically suppresses transcription of the avian erythrocyte anion transporter (band 3) gene. Cell 1988 Jan. 15; 52(1): 107–19. ¶ 29, pp. 15–16.

Abstract–Zuk, R F, et al. Enzyme immunochomatography—a quantitative immunoassay requiring no instrumentation. Clin Chem 1985 Jul.; 31(7): 1144–50. ¶ 30, p. 16.

Abstract—Ionescu–Tirgoviste C, et al. Comparative study of insulin antibodies in diabetic patients with primary insulin–dependence (type I) and secondary insulin–dependence (type II). Clinic of Diabetes, Nutrition and Metabolic Diseases. Med Interne 1989 Oct.–Dec.; 27(4): 303–11. Unique Identifier 90140348, p. 1.

Abstract—Umezawa, S. [Urinary hGH, albumin, alpha 1 MG and beta 2 MG in normal and diabetic children]; Endocrine Research Lab., Nat'l Children's Med. Res. Ctr, Nippon Naibunpi Gakkai Zasshi 1989 Jan. 20; 65(1): 55–65. Unique Identifier: 89252264, p. 2.

Abstract—Makita, Z. [Radioimmunoassay for the determination of glycated hemoglobin and its clinical significance; Second Dept. of Internal Med., Hokkaido Univ. School of Med., Sapporo, Japan. Hokkaido Igaku Zasshi 1989 1989 Jan.; 64(1): 65–74. Unique Indentifier: 89253272, p. 3.

Abstract—Moses, E K, et al. Molecular analysis of one of multiple protease–enclolding genes from the prototype virulent strain of Bacteroides nodosus. Gene 1989 Apr. 30; 77(2): 219–28. ¶ 1, p. 1 re Serine Protease.

Abstract—Paborsky, L R, et al. Purification of recombinant human tissue factor. Biochemistry 1989 Oct. 3; 28(20): 8072–7. ¶ 2, pp. 1–2.

Abstract—Turner, M W, et al. Mucosal mast cell activation patterns in the rat following repeated feeding of antigen. Clin Exp Allergy 1990 Jul.; 20(4): 421–7. ¶ 3, p. 2.

Abstract—Cabrini, G, et al. An evaluation of an enzyme immunoassay method for immunoreactive trypsin in dried blood spots. Clin Biochem 1990 Jun.; 23(3): 213–9. ¶1, p. 1.

Abstract—Castels E, et al. NCI–H292 as an alternative cell line for the isolation and propagation of the human paramyxovieuses. Arch Virol 1990; 115(3–4): 277–88. ¶ 2, pp. 1–2.

Abstract—Hesselvik, F, et al. Influence of plasma protease activation on electroimmunoassay and nephelometry of plasma fibronectin in sepsis. Throm Res 1989 Dec. 15; 56(6): 731–7. ¶ 3, p. 2.

Abstract—Marsigliante, S, et al. Significance of the 8S complex in oestrogen receptor recognition. J Sterod Biochem Mol Biol 1991 Nov.; 39 (5A): 703–11. ¶ 4, p. 3.

Abstract—Molchanova To, et al. [The low–molecular protein of the cell wall in streptococci group A devoid of serological type specificity]. Zh Mikrobiol Epidemiol Immunobiol 1991 Feb.; (2): 16–20. ¶ 5, p. 4.

Abstract—Nartikova V, et al. [Shigella endotoxin protein—its electrophoretic and serological properties]. Zh Mikrobiol Epidemiol Immunobiol 1991 Apr.; (4): 14–7. ¶ 6, pp. 4–5.

Abstract—Sakakibara K, et al. Urinary UK, t–PA and urinary trypsin inhibitor in health and glomerular diseases. Throm Res 1989 Oct. 15; 56(2): 239–49. ¶ 7, p. 5.

Abstract—Buchler M, et al. Cholecystokinin influences pancreatic trophism following total gastrectomy in rats. Int J. Pancreatol 1989 Apr.; 4(3): 261–71. ¶ 1, p. 1.

Abstract—Berger Z, et al. Prostaglandin F2 alpha and prostacyclin tissue levels in early phases of trypsin–induced acute pancreatitis in rats. Pancreas 1989; 4(3): 295–9. ¶ 2, pp. 1–2.Abstract—Nartikova V, et al. [Shigella endotoxin protein—its electrophoretic and serological properties]. Zh Mikrobiol Epidemiol Immunobiol 1991 Apr.; (4): 14–7. å 6, pp. 4–5.

Abstract—Sakakibara K, et al. Urinary UK, t–PA and urinary trypsin inhibitor in health and glomerular diseases. Throm Res 1989 Oct. 15; 56(2): 239–49. å 7, p. 5.

Abstract—Buchler M, et al. Cholecystokinin influences pancreatic trophism following total gastrectomy in rats. Int J. Pancreatol 1989 Apr.; 4(3): 261–71. å 1, p. 1.

Abstract—Berger Z, et al. Prostaglandin F2 alpha and prostacyclin tissue levels in early phases of trypsin–induced acute pancreatitis in rats. Pancreas 1989; 4(3): 295–9. å 2, pp. 1–2.

Abstract—Cabrini, G, et al. An evaluation of an enzyme immunoassay method for immunoreactive trypsin in dried blood spots. Clin Biochem 1990 Jun.; 23(3): 213–9. å 3, p. 2.

Abstract—Dores, R M, et al. Detection of Met–enkephalin and Leukenkephalin in the posterior pituitary of the holsteam fish, Amia calva. Peptides 1989 Sep.–Oct.; 10(5): 951–6. å 4, p. 3.

Abstract—Dymshitz, J, et al. Coculture of anterior and posterior pituitary cells: selective stimulation of lactotrophs. Endocrinology 1991 May; 128(5): 2469–75. å 5, pp. 3–4.

Abstract—Fitzpatrick L A, et al. Individual parathyroid cells are more sensitive to calcium than a parathyroid cell population. Endocrinology 1990 Mar.; 126(3); 1720–7. å 6, p. 4.

Abstract—German S V, et al. [Immunoreactive trypsin in the blood serum of patients with endogenous hypercorticism]. Klin Med (Mosk) 1990 Jun.; 68(6): 112–5. å 7, p. 5.

Abstract—Glasbrenner, B, et al. Effects of TRH on pancreatic growth and secretion in rats. Pancreas 1990; 5(1): 37–41. å 8.

Abstract—Kulis, W, et al. Differential processing of proenkephalin–A by human peripheral blood monocytes and T lymphocytes. J Clin Invest 1991 Sep.; 88(3): 817–24. å 9, p. 6.

Abstract—Lewis, U J, et al. Two forms of glycosylated human prolactin have different pigeon crop sac-stimulating activities. Endrocrinology 1989 Mar.; 124(3): 1558–63. å 10, pp. 6–7.

Abstract—Lucas, D, et al. Release in vivo of Met–enkephalin and encrypted forms of Met–enkephalin from brain and spinal cord of the anesthetized cat. Peptides 1990 Nov.–Dec.; 11(6): 1119–25. å 11, p. 7.

Abstract—Ohno, I, et al. Fc receptors for IgE (Fc epsilon R) on human ;ymphoid cells: inducible expression of Fc epsilon RII (CD23) on lymphocytes and detection by monoclonal anti–Fc epsilon RII antibody. Cell Immunol 1989 Jul.; 121(2): 433–46. å 12, p. 8.

Abstract—Oza, N B, et al. Rat aortic smooth muscle cells in culture express kallikrein, kininogen, and bradykininase activity. J Clin Invest 1990 Feb.; 85(2):597–600. å 13, pp. 8–9.

Abstract—Richoux, J P, et al. The Kallikrein–kinin system in the rat hypothalamus. Immunohistochemical localization of high molecular weight kininogen in different neuronal systems. Histochemistry 1991; 96(3): 229–43. å 14, pp. 9–10.

Abstract—Roxvall, L, et al. Activation of the complement cascade by trypsin. Biol Chem Hoppe Seyler 1991 Apr.; 372(4): 273–8. å 15, p. 10.

Abstract—Sarfati, P, et al. evidence of a new serin protease in the rat pure pancreatic juice that degrades somatostatin. Life Sci 1990; 47(12): 1043–9. å 16, pp. 10–11.

Abstract—Scheuring, U, et al. Analysis of pancreatic serum markers in patients with cyctic fibrosis. Pancreas 1991 Mar.; 6(2): 229–33. å 17, p. 11.

Abstract—Shibata, T, et al. Compement activation induces the expression of decay–accelerating factor on human mesangial cells. J Immunol 1991 Dec. 1; 147(11): 3901–18. å 18, pp. 11–12.

Abstract—Slifman, N R, et al. Human eosinophil–derived neurotoxin and eosinophil protein X are likely the same protein. J Immunol 1989 Oct. 1; 143(7): 2317–22. å 19, p. 12.

Abstract—Stell, W K, et al. Detection of synenkephalin, the amino–terminal portion pf proenkephalin, by antisera directed against its carboxyl terminus. J. Neurochem 1990 Feb.; 54(2):434–43. å 20, p. 13.

Abstract—Sun, M. [Effects of alpha–human ANF and Angiotensin II on aldosterone secretion in vitro from cultured human adrenal tissues and APA tissues]. Chung Hua Hsin Hsueh Kuan Ping Tsa Chih 1990 Apr.; 18(2): 87–90, 126. å 21, p. 14.

Abstract—Toresson, G, et al. Neuropeptide K is present in human cerebrospinal fluid. Life Sci 1990; 46(23):1707–14. ¶ 22, pp. 14–15.

Abstract—Ebeling, F. Alanine aminotransferase, gamma-glutamyltransferase, antibodies to hepatitis B core antigen and antibodies to hepatitis C cirus in blood donor screening. A prospective study in Finland. Vox Sang 1991; 60(4):219–24. Unique Ident.: 920241777, p. 1.

Abstract—Hadley, S P, et al. Effect of glucocorticoids on alkaline phosphatase, alanine aminotransferase, and gammaglutamyltransferase in cultured dog hepatocytes. Dept. of Vet. Pathobio. College of Vet. Med., Univ. of Ill. Enzyme 1990; 43(2):89–98. Unique Ident. 91085418, p. 2.

Abstract—Asahina, T, et al. [Studies on the immunohistochemical localization of adhesive factors at the site of implantation in the early pregnancy]. Dept. of Obstetrics and Gynecology, Hamamatsu Univ. School of Med. Nippon Sanka Fujinka Gakkai Zasshi 1990 Sep; 42(9):1168–74. Unique Identifier: 91011039, p. 3.

Abstract—Lopatakin, N A, et al. [The differential diagnosis of allergic prostatitis]. Language: Russian. Urol Nefrol (Mosk) 1990 Mar–Apr; (2):17–20. Unique identifier: 90312735, p. 4.

Abstract—Blick, K E, et al. A validation study of selected methods routinely used for measurement of cyclosporine. Department of Pathology, Univ. of Okalahoma Health Sciences Center, Oklahoma City 73126. Clin Chem 1990 Apr; 36(4):670–4. Unique identifier: 90213863, p. 5.

METHODS AND KITS FOR DETECTING THE PRESENCE OR CONCENTRATION OF BIOLOGICAL ANALYTES

This application is a continuation of application Ser. No. 08/027,549 filed Mar. 8, 1993, now abandoned, which is, in turn, a continuation of Ser. No. 07/832,429, filed Feb. 7, 1992, now abandoned.

BACKGROUND OF THE INVENTION

The present invention relates to methods for detecting the presence or concentration of a biological analyte in a matrix, such as urine or blood, by exploiting the specificities of an antibody and a signal-generating substrate for the analyte. More particularly, the present invention relates to methods for detecting the presence or concentration of an analyte, such as hemoglobin or a transferase or a serine protease, in a matrix by exploiting the antibody specific to the analyte to extract the analyte from its matrix, and by exploiting the substrate specific to the enzymatic property of the analyte in order to generate a signal proportionate to the amount of analyte in the matrix.

The known in vitro methods for directly detecting the presence or concentration of an analyte in a matrix using its specificity for its substrate have several disadvantages. Often, for instance, the matrix may contain substances which may interfere or inhibit direct testing for the analyte, thereby giving false positive or negative indications. Also, if the matrix is slightly hemolyzed, it may interfere with the measurement of light absorbance during spectrophotometric analysis. Likewise, any turbidity in the matrix will also obstruct the measurement of light absorbance during spectrophotometric analysis.

The known methods for testing hemoglobin in a matrix readily identify the disadvantages of such techniques. In particular, since hemoglobin acts as a pseudoperoxidase enzyme, known methods for directly testing a sample for hemoglobin have utilized hydrogen peroxide as a substrate. If hemoglobin is present in the matrix, it will liberate from hydrogen peroxide nascent oxygen which in turn oxidizes an added colorless dye into a colored form. However, the matrix being tested for hemoglobin may contain interfering substances, such as urine containing vitamin C or glutathione or their metabolites which may inhibit oxidation of the colorless dye. Thus, a false negative result may be obtained. Also, the matrix may contain interfering substances which give the same reaction as hemoglobin. For example, a feces sample containing vegetable peroxidase may react like hemoglobin when directly tested by the use of a peroxide substrate and colorless dye. Accordingly, in this situation, a false positive indication for the presence of hemoglobin may be obtained.

The presence of hemoglobin or its isoforms in a matrix has also been determined by various immunoassays known in the art. One such method captures the hemoglobin molecules by binding them to an antibody attached to a solid surface, and then enumerates the molecules by binding them with yet another antibody that is enzyme labeled. Alternatively, in other known methods, a second antibody is bound to the captured hemoglobin and is enumerated by an enzyme-labeled, third antibody. Thus, these types of immunoassays ignore the specific substrate for the enzymatic, or pseudoperoxidase property of the hemoglobin molecule and instead require the need for a secondary (or tertiary) antibody label.

Similar problems and disadvantages are encountered with the known methods used to test for gamma-glutamyl transferase enzyme (or "GGT"). For example, known methods for directly testing a matrix for GGT by utilizing a signal-generating specific substrate are also subject to interferences by other substances in the matrix. Substances such as citrate, oxalate, and fluoride are known to suppress GGT enzyme activity, thereby giving falsely low values in the measurement of light absorbance in a spectrophotometer. In addition, if the sample or matrix is slightly hemolyzed, it may absorb light in the same or close wavelength range as the GGT-substrate signal, thereby artificially increasing light absorbance and giving a false positive value.

Accordingly, there has existed a definite need for a method of testing for the presence or concentration of an analyte in a matrix which overcomes these disadvantages. Specifically, there is a need for a method which exploits the antibody specificity of the analyte to avoid the possible interferences of other substances contained within the matrix, and which exploits the substrate specificity of the enzymatic property of the analyte to generate a signal to indicate the analyte's presence or concentration. The present invention satisfies these needs and provides further related advantages.

SUMMARY OF THE INVENTION

The present invention relates to in vitro methods for detecting the presence or concentration of an analyte contained within a matrix, such as urine or blood. More specifically, the method of the present invention first extracts the analyte from the matrix by binding it with an antibody attached to a solid surface. The antibody-bound analyte is then separated from the unreacted analyte and matrix. A substrate is then added which is specific to the enzymatic property or activity of the analyte. The substrate is capable of generating a signal (such as a change in absorbance or color) that is proportionate to the amount of the analyte bound to the antibody (and which in turn is dependent on the amount of the analyte present in the matrix.) The generated signal is then detected or measured by a spectrophotometer and the presence or concentration of the analyte is determined in comparison with the measurements of samples of known concentrations.

Thus, the present invention provides a method to extract an analyte from a matrix where intrinsic substances may interfere with its detection and quantification. Further, extraction of the analyte from the matrix by binding it with its specific antibody also preserves the enzyme-substrate activity of the analyte. This allows the specific substrate for the enzymatic property of the analyte to be utilized in order to generate a signal to indicate its presence or concentration. Thus, the need for a secondary or tertiary label is avoided (e.g., a second or third antibody labeled with enzyme or fluorescein, etc.) The present invention also provides for a reliable test since the specificity of the antibody for the analyte is enhanced by the specificity of the substrate for the antibody-bound analyte.

The present invention is also embodied in kits to employ the methods of the present invention. The kits include an antibody specific to the particular analyte desired to be tested for, and the substrate specific for the enzymatic property of the analyte, which is capable of generating a measurable signal. The kits may further include the necessary reagents to carry out the methods of the present invention.

Other features and advantages of the present invention will become apparent from the following detailed description, taken in conjunction with the accompanying figures, which illustrate, by way of example, the principles of the invention.

BRIEF DESCRIPTION OF THE DRAWINGS

The accompanying drawings illustrate the invention. Specifically.

DETAILED DESCRIPTION OF THE PREFERRED EMBODIMENT

Figure 1:
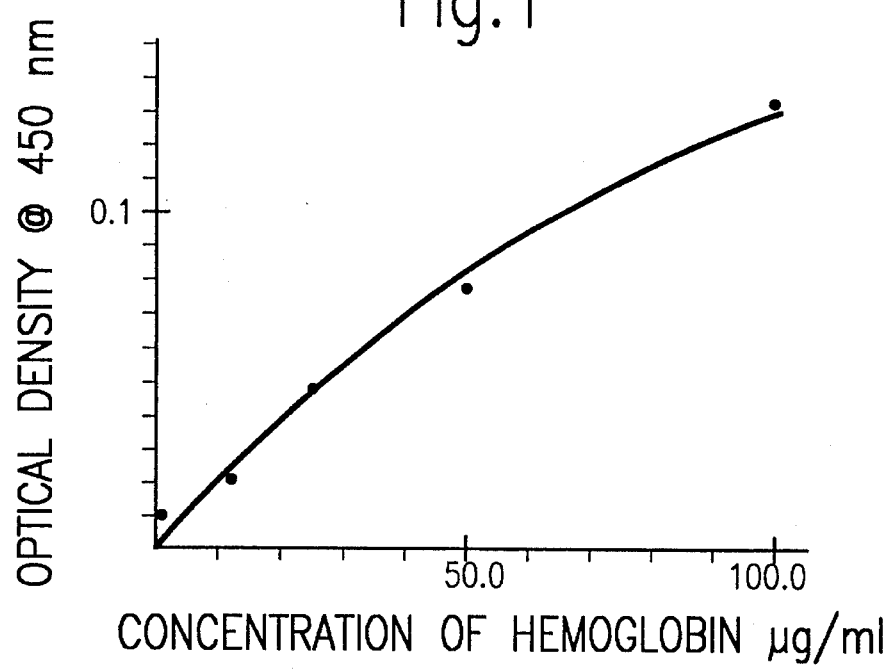
FIG. 1 is a representative graph of optical density readings of tested samples of known concentrations of hemoglobin A1C.

The present invention provides in vitro methods for detecting the presence and concentration of an analyte by exploiting the specificity of an antibody for the analyte, and the specificity of a substrate for the enzymatic property of the analyte. The methods of the present invention are advantageous, for instance, for detecting the presence or concentration of analytes of clinical diagnostic relevance and capable of giving a signal with a particular substrate, such as hemoglobin or gammaglutamyl transferase enzyme (GGT) or the serine protease trypsin, in matrices, such as urine, feces, or other bodily fluids per se, or in a fluid dried into a solid matrix whence it can be eluted into a biological buffer for analysis. Other enzymes which may be tested by the methods of the present invention include, but are not limited to, asparate aminotransferase ("AST") (EC 2.6.1.1), alanine aminotransferase (EC 2.6.1.2) (ALT), serine proteases such as trypsin (EC 3.4.21.4) and chymotrypsin (EC 3.4.21.1), creatin N-phosphotransferase (CK) (EC 2.7.3.2), aldolase, lactate dehydrogenase, isocitrate dehydrogenase, alkaline phosphatase, acid phosphatase, terminal deoxynucleotidyl transferase, biliary tract enzymes including 5'-Nucleotidase, and digestive enzymes of pancreatic origin including amylase, lipase, and cholinesterase. (The EC numbers designate the international enzyme nomenclature classifications of the particular enzymes.) It should be appreciated, however, that the methods of the present invention are not limited to the testing of the above-mentioned analytes, and that the present invention encompasses the testing of other amenable analytes, or analytes having enzyme or enzyme-like activity and capable of generating signals with their specific substrates.

The method of the present invention first extracts the analyte from the matrix involved by binding the analyte to its specific antibody which is attached to a solid surface, such as the surface of a microwell. The antibody-bound analyte is then separated from the matrix and unreacted analyte by washing it off with deionized water or buffered solutions with or without the help of detergents. As a result, the analyte is removed from any substances contained in the matrix which may later interfere with its detection.

The next step in the method of the present invention, therefore, exploits the specificity of a substrate for the enzymatic property of the analyte to generate a measurable signal, such as a change in absorbance or color, to determine the presence or concentration of the analyte. The signal or optical density of the resulting solution is then read by a spectrophotometer, or visually estimated for qualitative results.

The method thus takes advantage of the signal-giving, enzymatic property of the analyte itself, thereby eliminating the need for a secondary label, such as a second antibody labeled with an enzyme or fluorescein. Further, besides providing for a test which is essentially free from matrix interferences, the method of the present invention also advantageously provides for a more specific test due to the fact that the antibody specificity of the analyte is further enhanced by the specificity of the substrate for the antibody-bound analyte.

One embodiment of the present invention involves the determination of the presence or concentration of hemoglobin (or one of its isoforms, hemoglobin A1C or AO) in a matrix. First, it should be noted that hemoglobin acts as a pseudoperoxidase, an enzyme which liberates from hydrogen peroxide nascent oxygen, which in turn can generate a signal by oxidizing a leucodye, or colorless dye, into a colored form.

The advantages of this method for detecting the presence or concentration of hemoglobin in a matrix are many. First, the extraction of the hemoglobin from the matrix eliminates substances which interfere with the signal-giving, pseudoperoxidase property of hemoglobin. For instance, vitamin C or glutathione, which may be present in the matrix being tested, may inhibit oxidation, thereby masking the pseudoperoxidase property of hemoglobin and giving a false negative result. Also, during direct enzymatic testing, substances present in the matrix, such as vegetable peroxidase in feces may give the same reaction as the pseudoperoxidase property of hemoglobin, thereby generating a false positive signal. The present invention therefore removes the hemoglobin from the matrix to eliminate the risk of interferences, and then utilizes its pseudoperoxidase-substrate specificity to generate a signal.

Another embodiment of the method of the present invention involves its application for detecting a transferase, specifically gammaglutamyl transferase enzyme (GGT) in a matrix or sample. The detection of elevated levels of serum GGT has proven useful in identifying diseases of the liver, bile duct, and pancreas. The presence of GGT is currently tested using enzyme-substrate specificity without any antibody extraction of the GGT from the serum sample or matrix. Such procedures for determination of GGT are described in TEXTBOOK OF CLINICAL CHEMISTRY by Norbert W. Teitz, W. B. Sanders, Philadelphia, Pa., 1986.

As discussed in more detail below, by using the method of the present invention, GGT is first extracted from its matrix by binding it with its specific antibody coated on a solid surface. After the test matrix has been incubated and allowed to fully react with the antibody, the unreacted GGT and matrix are aspirated and washed off, thereby leaving the antibody-bound GGT on the solid surface. The GGT is thus removed from its matrix and from any substances which may interfere with its detection. For instance, if the GGT is not extracted from its matrix, substances such as citrate, oxalate, and fluoride may interfere or suppress its enzyme activity during specific enzyme-substrate testing giving falsely low values in a spectrophotometric analysis. Also, if the matrix is slightly hemolyzed, or if there is any turbidity in the sample, the measurement of light absorbance in a spectro-photometer may be artificially increased or decreased giving false values. Thus, the method of the present invention avoids these potential problems by extracting the GGT from the sample or matrix before specific enzyme-substrate testing.

Once removed from its matrix, the presence of antibody-bound GGT is determined by contacting it with its specific enzyme-substrate and particular reagents in solution. The signal or color change, if any, generated by the reaction of the antibody-bound GGT and GGT specific substrate is then read in a spectrophotometer and compared to readings of known concentrations in order to determine the amount of GGT in the matrix. (The preparation of a known concentration curve is discussed below.)

A further embodiment of the present invention involves the detection and quantification of a serine protease, namely trypsin, in a matrix or sample by exploiting the antibody specificity and substrate specificity for the serine protease.

In another aspect of the present invention, kits for measuring the presence or concentration of analytes by the methods of the present invention are provided. The kits of the present invention contain antibodies for the particular analyte to be tested. The antibodies are attached to a solid surface, such as microwells. The kits also include a signal-generating substrate which is specific to the enzymatic property of the analyte to be tested. In addition, other materials such as reagents may be included with the kits to carry out the methods of the present invention.

In the preferred embodiments of the present invention, the antibodies are attached to a solid surface. The term "solid surface" refers to any support useful in immunometric assays, and can be made from materials or synthetic materials which are insoluble in water, such as polyethylene, polystyrene, nylon, nitrocellulose, glass microfibers, or magnetic materials. In addition, the solid surface should not significantly affect the desired activity of the specific antibodies or substrates used for the analyte being tested. Preferred solid surfaces include, but are not limited to, beads, flat dipsticks, test tubes, test wells or microwells. Any method known in the art to attach the antibodies to the solid surfaces can be used.

As used herein, the term "reagent" refers to the washing buffers, solutions, or any other component useful to perform the assays of the present invention.

The antibodies useful with the present invention can be obtained by techniques well known in the art. Such antibodies can be polyclonal or monoclonol.

The term "sample" or "matrix" refers to any substance or solution containing an analyte, or arrived at after preliminary procedures such as elution (if blood was dried on a solid matrix) or dilution after lysis of cells. A sample or matrix can be obtained from any biological fluid, for example, whole blood, plasma, urine or feces.

The term "analyte" or "biological analyte" refers to or means any substance having enzyme or enzyme-like activity and whose presence or concentration in a matrix or sample can be tested by the methods of the present invention. The term includes substances which can be extracted from a matrix by binding it with its specific antibodies, and which is capable of giving a measurable signal to determine its presence or concentration when reacted with its specific substrate.

The term "substrate" or "specific substrate" or "specific enzyme-substrate" refers to or means any substance, compound, solution, element, or the like which generates a detectable or measurable signal (such as a change in absorbance or color) by reacting with or exploiting the enzymatic property of an analyte, such that the presence or concentration of the analyte in a matrix or sample can be determined.

The following examples are intended to illustrate and not limit the methods and applications of the present invention.

EXAMPLE I

HEMOGLOBIN ENZYME IMMUNOASSAY

A. Binding of the Antibody to a Solid Surface

A polystyrene, 96-microwell microtiter plate is washed with distilled water at room temperature. (It should be understood that the solid surface can take other forms such as a bead, or flat dipstick, and can be made from other materials such as plastic, glass, glass fiber, magnetic material, steel, nylon polycarbonate, nitrocellulose, or the like.) Anti-hemoglobin A1C antibody is diluted to a 1% solution in phosphate buffered saline ("PBS") (pH 7.4) containing 0.1% sodium azide. (Anti-hemoglobin A1C antibody is available from Biodesign, Inc.) The buffer system could also be a bicarbonate buffer, or Tris buffered saline. 100 ul of the anti-hemoglobin A1C solution is then added to each microwell. After 18 hours of incubation at room temperature, the antibody solution is aspirated from the wells which are then washed with distilled water. (The incubation period can vary from 2 hours at 37° C. to 48 hours at room temperature.)

In order to block unbound sites on the solid surface of the microwell, 250 ul (u=micro) of 2% weight by volume (w/v) bovine serum albumin (BSA) in PBS (pH 7.4) is added to each microwell where it is allowed to react for 18 hours at room temperature. It should be noted that any other suitably inert protein may be used instead of BSA, such as gelatin. Finally, after 18 hours has passed, the microwells of the microtiter plates are aspirated and washed with distilled water to eliminate unreacted BSA.

B. Assay Procedure

In order to analyze an actual matrix or sample, optical density readings from a spectrophotometer for known concentrations of pure hemoglobin A1C are prepared. (This known concentration analysis is later used to determine the concentration of the particular analyte tested based on its optical density signal.) This may be accomplished by adding a known amount of pure hemoglobin A1C to a liquid matrix of 2% w/v BSA in a PBS of pH 7.4. In the present example, separate known samples of the following concentrations of pure hemoglobin A1C in a BSA matrix are prepared—100 ug/ml, 50 ug/ml, 25 ug/ml, 12.5 ug/ml, 1.25 ug/ml, and 0 ug/ml (u=micro).

Each of the known samples (in amounts of 100 ul) is incubated in a separate antibody-coated microwell for 18 hours at 37° C., and rotated at 120 rpm. The unreacted sample in each microwell is washed off with deionized water. Next, a substrate specific to the enzyme activity of the antibody-bound hemoglobin A1C is added to each microwell. Hemoglobin is a pseudoperoxidase, since it acts as a peroxidase enzyme which liberates from hydrogen peroxide nascent oxygen, which in turn can oxidize a colorless dye or leucodye, such as tetramethyl benzidine, to give a color signal. The source of the peroxide may be aqueous such as hydrogen peroxide dissolved in water, or organic such as cumene hydro peroxide or benzoyl hydro peroxide. The peroxide may also be produced in situ, for example, by coating the solid surface of the microwell with glucose oxidase in BSA to which a solution of glucose is added along with the leucodye. Other suitable leucodyes or chromagenic compounds can be used including diaminobenzidine, 4-chloro-1-naphtol, 0-tolidine, phenolphthalein, malachite green, 4-aminoantipyrine, guaiacol, purpurogellin, pyrogallol, 0-phenylenediamine, 2,2'-azino-di (3-ethylbenzthiazoline sulphonic acid-6) or ("ABTS"), 0-dianisidine and 4-aminoantipyrine.

Thus, in this particular example, 100 ul of a hydrogen peroxide solution and 100 ul of a tetramethyl benzidine solution are added to each microwell. More specifically, the hydrogen peroxide solution is comprised of 0.03% hydrogen peroxide in an acetate buffer (of pH 5.0 and 0.05 M). The tetramethyl benzidine solution consists of 600 micrograms of tetramethyl benzidine per milliliter of acetate buffer (0.05 M) containing 20% volume by volume (v/v) of dimethyl sulfoxide and 10% v/v of dimethyl formamide. The microtiter plate is then covered and rotated at 120 rpm. The reaction is then stopped by adding 100 ul of a stop solution (or 1N HCl). Stopping the reaction is not necessary if only a qualitative result, or a color change indicating the presence of the analyte in a matrix, is desired. The optical density of the color indication signal of each known sample is then read at 450 nanometer (nm) wavelength in a spectrophotometer.

The optical density readings for each known sample are then plotted against the concentrations to achieve a known dose or concentration response curve as shown in FIG. 1. The values for the known concentration response curve of FIG. 1 were obtained by running an experiment in accordance with the above example. The particular readings are as follows:

TABLE 1

| Sample Concentration (ug/ml) | Net Optical Density |
|---|---|
| 0 | 0.0 |
| 1.25 | 0.010 |
| 12.5 | 0.021 |
| 25.0 | 0.050 |
| 50.0 | 0.081 |
| 100.0 | 0.139 |

This particular experiment utilized an antibody specific to hemoglobin A1C, an isoform of hemoglobin. It should be appreciated by one of skill in the art that various isoforms of hemoglobin, such as hemoglobin AO or hemoglobin A1C, give reactions with the substrate after binding with the antibody.

Further, it shall be noted that the optical density readings given in Table No. 1 are net values. The net values are derived by subtracting a standard optical density reading of the spectrophotometer from the raw optical density readings taken by the spectrophotometer. The standard optical density value is evaluated by measuring the optical density reading of a blank in the spectrophotometer.

It should now also be appreciated that if the particular antibody used has a high affinity for the hemoglobin, then the antibody can be diluted to 1:1000 or further in PBS, rather than 1:100 as described above, so that lower optical density readings are obtained. Similarly, if the particular antibody has a low affinity for the hemoglobin, the antibody should only be diluted to a lesser extent, such as 1:50.

The unknown sample is tested in the same way as the known samples and can be tested at the same time as the known samples. First, 100 ul of the matrix is incubated in an antibody-coated microwell for 18 hours at 37° C. and rotated at 120 rpms. The unreacted matrix is washed off with deionized water. Afterwards, 100 ul of the hydrogen peroxide solution and 100 ul of the tetramethyl benzidine solution, as prepared above, are added to the microwell. The plate is covered and rotated at 120 rpm. The reaction is stopped using 100 ul of the HCl stop solution, and the optical density signal of the sample is read in a spectrophotometer at a wavelength of 450 nm. Using the known concentration curve as shown in Table 1, it should be appreciated that the concentration of the hemoglobin can then be determined.

EXAMPLE II

GAMMAGLUTAMYL TRANSFERASE IMMUNOASSAY

A. Binding of the Antibody to the Substrate

This example pertains to the detection and quantification of a transferase, and in particular, gammaglutamyl transferase. The binding of the antibody to the substrate is very similar to the above procedures used for the hemoglobin immunoassay described above, with a few exceptions as noted below.

First, a polystyrene, 96-microwell microtiter plate is washed with distilled water. Next, 100 ul of rabbit, anti-human gammaglutamyl transferase (GGT) antibody is added to each microwell after diluting it to 1% (w/v) in PBS (pH 7.4) containing 0.1% sodium azide. The antibody may be raised in any animal species other than humans. The anti-GGT antibody is incubated in the microwells for 18 hours at room temperature. However, the duration and temperature can vary from 2 hours at 37° C. to 48 hours at room temperature.

The microwells are then aspirated and washed with distilled water. The uncoated sites on the surface of each microwell are blocked using 300 ul of 2% w/v BSA in PBS (pH 7.4) or any inert protein like gelatin, or non-immune IgG. The solution is allowed to react with the surface of the microwells overnight at room temperature. The excess BSA is then aspirated and washed off with deionized water.

For the examples provided, it should be appreciated that the time, temperature and concentration of the antibody or the buffer solution of the antibody may be varied to suit individual needs or characteristics of the antibody. Similarly, the time, temperature or concentration of the BSA, or the inert proteins, and their buffer systems may be varied according to need.

B. GGT Assay Procedure

A known concentration analysis or curve is generated for various concentrations of pure GGT. For instance, known amounts of human GGT are added to 2% w/v BSA in PBS (pH 7.4) to obtain solutions having the following concentrations—4.87 units/L, 9.75 units/L, 19.5 units/L, 39.0 units/L, 78.0 units/L, 155 units/L and 310 units/L. It should be appreciated by one of ordinary skill in the art that "units" refer to the active concentration of the enzyme that participates in the reaction with the substrate. Each one of these known samples of human GGT (in amounts of 100 ul) is added to a separate microwell where it is allowed to react with the antibody-coated surface for a period of 18 hours at room temperature while being rotated in a hematology mixer at 120 rpm. (It should be understood that the duration, temperature and revolutions per minute may be varied to obtain the same results.)

The samples in the microwells are then aspirated and washed off with deionized water. Thereafter, 100 ul of freshly prepared GGT substrate is added to each microwell. The GGT substrate and reagents used in this example can be obtained from Sigma Diagnostics a division of Sigma Chemical Co., St. Louis. The GGT substrate solution is prepared by adding 11.0 ul of TRIZMA® buffer solution (0.1 moles/L, pH 9.0) (Sigma Diagnostics Catalog No. 545-2) to one vial of GGT substrate containing L-γ-glutamyl-p-nitroanilide, 51 umol, and glycylglycine, 1.1 mmol (Sigma Diagnostics Catalog No. 545-1). The GGT substrate in each microwell is incubated for 2½ hours at 37° C. After 2 hours, 50 ul of 1.7N, 10% v/v acetic acid (Sigma Diagnostics, Catalog No. 545-7) in deionized water, and 25 ul of 1.0% w/v sodium nitrite in deionized water (stored in a brown bottle) are added to each microwell. The microtiter plate is then allowed to mix for 3–5 minutes at room temperature.

Figure 2:
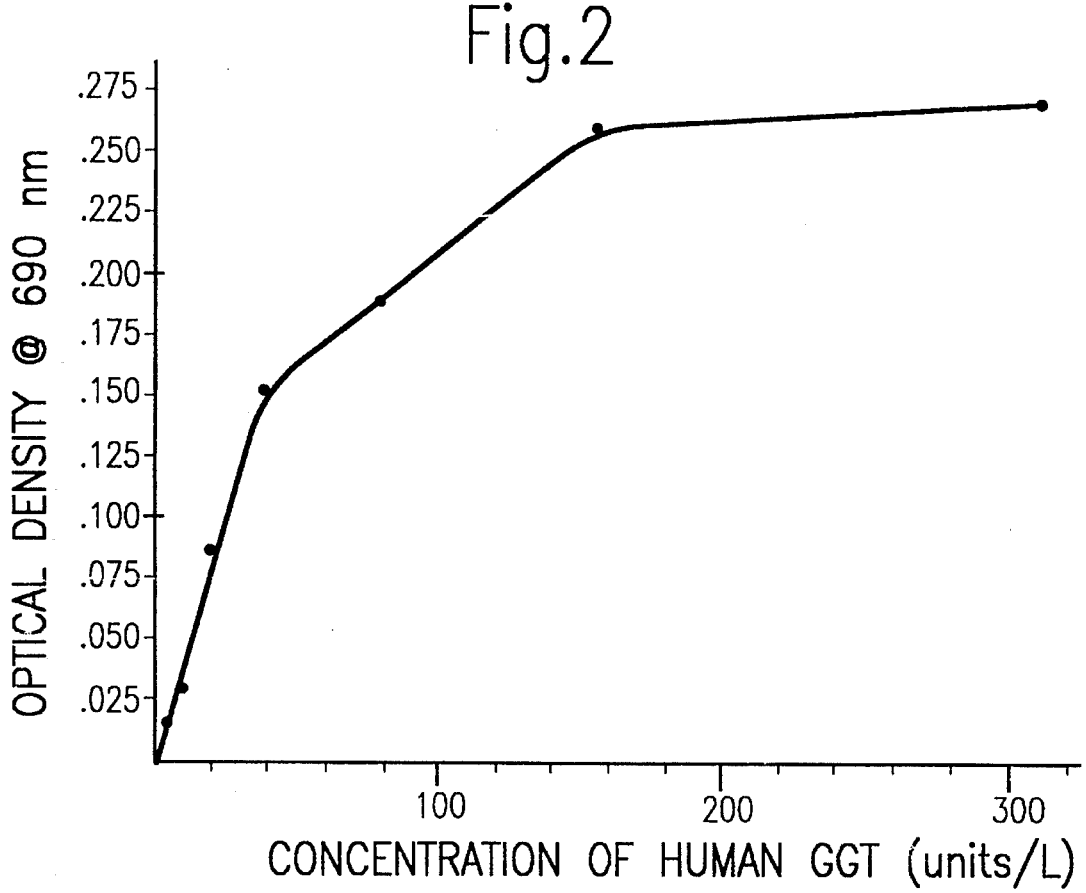
FIG. 2 is a representative graph of optical density readings of tested samples of known concentrations of gamma-glutamyl transferase enzyme.

Next, 50 ul of 1.0% w/v of ammonium sulfamate solution in deionized water (Sigma Diagnostics, Catalog No. 545-4), and 50 ul of N-1-Naphthylethylenediamine DiHCl solution (Sigma Diagnostics Catalog No. 251-5) are then sequentially added to each microwell. The N-1-Naphthylethylenediamine solution is prepared by adding 105 ml of water to a 55 mg bottle of N-1-Naphthylethylenediamine. The microtiter plate is then gently rotated for 1–3 minutes on a hematology mixer. The optical density signals for each known sample are read at 540 nm wavelength in a spectrophotometer, and the values plotted against the concentrations. The values for the known concentration curve of FIG. 2 were obtained by running an experiment in accordance with the above example. The particular readings are as follows:

TABLE 2

| Sample Concentration (Units/L) | Net Optical Density |
| --- | --- |
| 4.87 | 0.016 |
| 9.75 | 0.030 |
| 19.5 | 0.087 |
| 39.0 | 0.152 |
| 78.0 | 0.188 |
| 155.0 | 0.259 |
| 310.0 | 0.269 |

An unknown sample is tested in the manner similar to the known samples. The signal is read or detected and the concentration is determined by comparison to the known concentration curve.

EXAMPLE III

BOVINE TRYPSIN ENZYME IMMUNOASSAY

A. Binding of the Antibody to a Solid Surface

The present invention is also illustrated by its application to detect the presence and concentration of a serine protease, namely bovine trypsin, in a matrix.

Rabbit, anti-human trypsin (obtained from Ventrex Laboratories, Portland, Me.) is diluted to a 1% w/v solution in PBS (pH 7.4), containing 0.1% sodium azide. 100 ul of the diluted antibody solution is added to each microwell of a microtiter plate (from Costar of Cambridge, Mass.) and allowed to stand covered at room temperature at 25° C. for 18 hours. The solution is then removed and the microwells washed with distilled water two times.

Afterwards, in order to block unbound sites on the surface of the microwell, 250 ul of 2% w/v BSA in PBS (pH 7.4) containing 0.1% w/v sodium azide is contacted with the surface of the microwells and allowed to stand at 37° C. for two hours. The plates are kept covered during this time. (The 2% BSA in PBS solution is made by combining 8.0 ml of 30% BSA with 112.0 ml of PBS (pH 7.4) containing 0.1% sodium azide.) At the end of the two hours, the 2% BSA in PBS solution is removed and the microwells are washed three times with distilled water. The water is drained out by inverting the plates.

B. Assay Procedure

Figure 3:
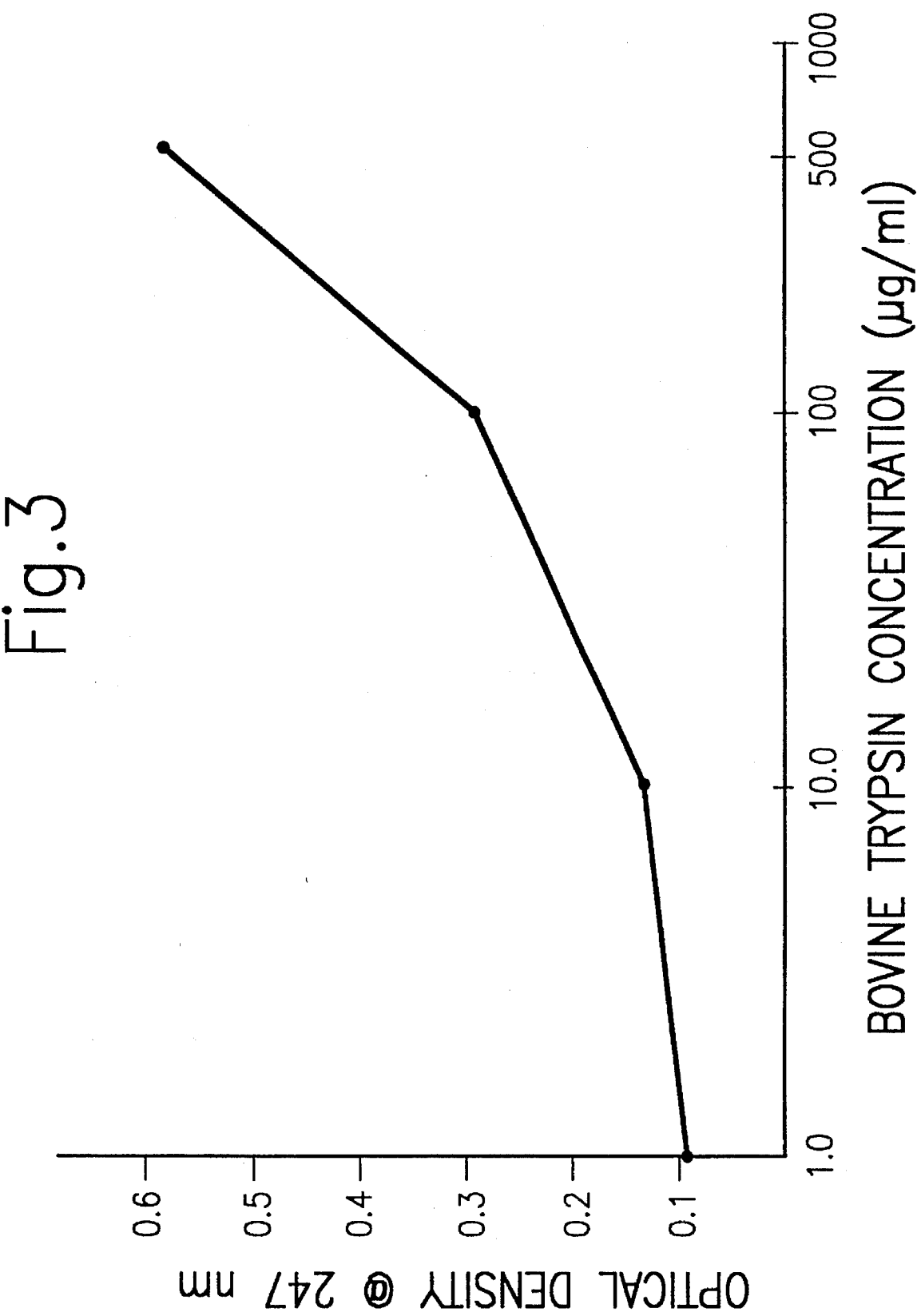
FIG. 3 is a representative graph of optical density readings of tested samples of known concentrations of bovine trypsin, a serine protease.

A known concentration analysis or curve is generated for various known concentrations of bovine trypsin. See FIG. 3. In particular, known amounts of bovine trypsin in solution having the following concentrations are used—1.0 ug/ml, 10.0 ug/ml, 100.0 ug/ml and 500.0 ug/ml. For example, to prepare a trypsin standard solution of 500 ug/ml, 20.1 mg of bovine trypsin (Sigma Chemical Co., St. Louis) is dissolved in 40.2 ml of 0.001N HCl in saline and diluted in 2% w/v BSA in Tris buffered saline (pH 7.0). (The 2% w/v BSA in Tris buffered saline is prepared by combining 4.25g of sodium chloride, 6.05g TRIZMA® base (from Sigma Chemical) and 10.0g of BSA, in 500 ml of distilled water. The pH of the solution is adjusted to pH 7.0.)

The known concentration samples are each placed in a separate microwell in 100 ul amounts. The samples are thus contacted with the anti-human trypsin antibody coated microwells and are allowed to react for 60 minutes at 4° C. Next, the unreacted samples are removed from the wells which are then repeatedly washed with distilled water (about 5 times.) Afterwards, 200 ul of the trypsin substrate solution TAME (0.0001M) (or p-toluene-sulfonylarginine methyl ester from Research Organics Inc. of Cleveland, Ohio) in 0.046M Tris HCl buffer (pH 8.1) containing 0.0115M calcium chloride is added to each microwell and allowed to react for 30 minutes at room temperature. Other trypsin substrates can be used such as: N-benzoyl-DL-arginine-p-nitroanilide (DL-Bapa) or (DL-Bapna); N-glutaryl-L-phenylalanine-P-nitroanilide (L-GPNA); benzoyl-L-arginine-ethyl ester (BAEE); and, P-nitrophenyl P-guanidino benzoate (NPGB). The reaction solution is read at 247 nm in a spectrophotometer and the optical density readings are recorded. The values for the known concentration curve of FIG. 3 were obtained by running an experiment in accordance with the above example. The particular readings are as follows:

TABLE 3

| Sample Concentration (ug/ml) | Net Optical Density |
| --- | --- |
| 1.0 | .084 |
| 10.0 | .134 |
| 100.0 | .307 |
| 500.0 | .596 |

An unknown sample is tested in the manner similar to the known samples. The signal is read or detected and the concentration is determined by comparison to the known concentration curve.

The foregoing description of the invention is exemplary for purposes of illustration and explanation. It will be apparent to those skilled in the art that changes and modifications will be possible without departing from the spirit and scope of the invention. It is intended that the following claims be interpreted to embrace all such changes and modifications.

I claim:

1. A non-competitive method of measuring the presence or concentration of an analyte in a matrix comprising:

(a) binding the analyte with an analyte-specific antibody attached to a solid surface, said analyte having enzymatic activity;

(b) separating the antibody-bound analyte from the unreacted analyte and matrix;

(c) reacting the antibody-bound analyte with a substrate specific to the enzymatic activity of the analyte in order to generate a measurable signal without the addition of other enzymes or labels; and (d) detecting the generated signal to determine the presence or concentration of the analyte.

2. The method for measuring the presence or concentration of an analyte in a matrix of claim 1, wherein the analyte is a hemoglobin.

3. The method for measuring the presence or concentration of hemoglobin in a matrix of claim 2, wherein the hemoglobin is an isoform of hemoglobin and the antibody is specific for that particular isoform.

4. The method of claim 3, wherein the hemoglobin isoform is A1C.

5. The method of claim 3, wherein the hemoglobin isoform is AO.

6. The method for measuring the presence or concentration of hemoglobin in a matrix of claim 2, wherein the substrate has a specificity for the pseudoperoxidase property of the antibody-bound hemoglobin.

7. The method for measurings the presence or concentration of hemoglobin in a matrix of claim 6, wherein the specific substrate is hydrogen peroxide.

8. The method for measuring the presence or concentration of hemoglobin in a matrix of claim 7, wherein a colorless dye is added to the hydrogen peroxide solution.

9. The method for measuring the presence or concentration of hemoglobin in a matrix of claim 8, wherein the colorless dye is a leucodye.

10. The method for measuring the presence or concentration of an analyte in a matrix of claim 1, wherein the analyte is a transferase.

11. The method for measuring the presence or concentration of an analyte in a matrix of claim 10, wherein the transferase is gammaglutamyl transferase.

12. The method for measuring the presence or concentration of gammaglutamyl transferase enzyme of claim 11 wherein the substrate is comprised of L-γ-glutamyl-p-nitroanilide and glyclyglycine in a buffer solution.

13. The method for measuring the presence or concentration of gammaglutamyl transferase enzyme of claim 12, further comprising adding solutions of acetic acid, sodium nitrite, ammonium sulfamate, and N-1-naphthylethylenediamine in sequence to the substrate to the substrate solution after it is added to react with the antibody-bound gammaglutamyl transferase.

14. The method for measuring the presence or concentration of an analyte in a matrix of claim 1, wherein the analyte is a serine protease.

15. The method for measuring the presence or concentration of an analyte in a matrix of claim 14, wherein the serine protease is trypsin.

16. A kit for non-competitive detection of the presence or concentration of an analyte, comprising:

(a) an antibody specific to the analyte attached to a solid surface, wherein the analyte has enzymatic activity; and (b) a substrate specific to the enzymatic activity of the analyte.

17. The kit for detecting the presence or concentration of an analyte of claim 16, wherein the antibody is a human anti-hemoglobin antibody.

18. The kit for detecting the presence or concentration of an analyte of claim 17, wherein the specific substrate is a hydrogen peroxide.

19. The kit for detecting the presence or concentration of an analyte of claim 16, wherein the antibody is anti-gammaglutamyl transferase antibody.

20. The kit for detecting the presence or concentration of an analyte of claim 19, wherein the specific substrate is comprised of L-γ-glutamyl-p-nitroanilide and glyclyglycine in a buffer solution.

21. The kit for detecting the. presence or concentration of an analyte of claim 20, further comprising solutions of acetic acid, sodium nitrite, ammonium sulfamate, and N-1-naphthylethylenediamine.

22. The kit for detecting the presence or concentration of an analyte of claim 16, wherein the antibody is an anti-trypsin antibody.

23. The kit for detecting the presence or concentration of an analyte of claim 22, wherein the substrate is specific to trypsin.

* * * * *